United States Patent
Tamames, III

(10) Patent No.: US 10,058,568 B2
(45) Date of Patent: Aug. 28, 2018

(54) TOXIN BINDING SYSTEM

(71) Applicant: Special Nutrients, Inc., Miami, FL (US)

(72) Inventor: Fernando Tamames, III, Key Biscayne, FL (US)

(73) Assignee: Special Nutrients, Inc., Miami, FL (US)

( * ) Notice: Subject to any disclaimer, the term of this patent is extended or adjusted under 35 U.S.C. 154(b) by 0 days.

(21) Appl. No.: 15/070,243

(22) Filed: Mar. 15, 2016

(65) Prior Publication Data

US 2016/0339056 A1 Nov. 24, 2016

Related U.S. Application Data

(60) Provisional application No. 62/164,819, filed on May 21, 2015.

(51) Int. Cl.
| | |
|---|---|
| *A61K 33/12* | (2006.01) |
| *A61K 33/06* | (2006.01) |
| *A01N 59/06* | (2006.01) |
| *A23K 20/28* | (2016.01) |
| *A61K 35/10* | (2015.01) |

(52) U.S. Cl.
CPC .............. *A61K 33/12* (2013.01); *A01N 59/06* (2013.01); *A23K 20/28* (2016.05); *A61K 33/06* (2013.01); *A61K 35/10* (2013.01)

(58) Field of Classification Search
CPC ........ A01N 59/06; A61K 35/10; A61K 33/12; A61K 33/06; A61K 2300/00; A23K 20/28
See application file for complete search history.

(56) References Cited

U.S. PATENT DOCUMENTS

| | | | |
|---|---|---|---|
| 3,586,478 A | 6/1971 | Neumann | |
| 5,639,492 A * | 6/1997 | Turk | ...................... A23K 20/28 426/2 |
| 5,935,623 A * | 8/1999 | Alonso-Debolt | ...... A23K 50/30 424/438 |
| 6,827,959 B1 | 12/2004 | Schall et al. | |
| 7,066,998 B2 | 6/2006 | Rohrbaugh et al. | |
| 8,507,019 B2 * | 8/2013 | Schoeters | ............ A23K 20/111 426/271 |
| 2009/0170705 A1* | 7/2009 | Nennemann | ........... A01N 25/08 504/367 |
| 2011/0281018 A1 | 11/2011 | Schoeters et al. | |

FOREIGN PATENT DOCUMENTS

WO     WO 91/13555     * 9/1991

OTHER PUBLICATIONS

Of Schaumberger et al. "Evaluation of the endotoxin binding efficiency of clay minerals using the Limulus Amebocyte lysate test: an in vitro study" in AMB Express, 2014, 4:1.*
Garcia-Sirera, Josep, "Endotoxins in swine-effects and strategies for control" International Pig Topics, vol. 25, No. 3, 2010, 4 pages.

* cited by examiner

*Primary Examiner* — Blessing M Fubara
(74) *Attorney, Agent, or Firm* — Meyertons, Hood, Kivlin, Kowert & Goetzel, P.C.

(57) ABSTRACT

In some embodiments, a composition and/or method may include a toxin binding system formulated for safe and effective mixture into various feed rations which are fed to monogastric and ruminant animals such as poultry, swine, cows, cattle, and fish, among others. The toxin binding system includes novel combinations of one or more of an organoclay, an activated hydrated sodium calcium aluminosilicate clay, and a synthetic hectorite clay. In some embodiments, the binding composition may include organoclay, bentonite, hectorite, Leonardite, and/or any combination thereof. The toxin binding complex may effectively bind mycotoxins, endotoxins and some pesticides in the animal's digestive system, preventing their absorption and the consequent damages to the animal. This binding action includes the T-2 toxin, which can start their damaging action in the animal's mouth, hence, offering protection from oral lesions.

12 Claims, No Drawings

TOXIN BINDING SYSTEM

PRIORITY CLAIM

This application claims priority to U.S. Provisional Patent Application No. 62/164,819 entitled "MYCOTOXIN BINDING SYSTEM" filed on May 21, 2015, all of which is incorporated by reference herein

BACKGROUND OF THE INVENTION

1. Field of the Invention

The present disclosure generally relates to a toxin binding system. More particularly, the disclosure generally relates to a toxin binding system which may be safely and effectively mixed into animal feed.

2. Description of the Relevant Art

Fungal contamination of animal feed is often unavoidable and is a serious concern given that many of these contaminants include toxic metabolites known as mycotoxins. Mycotoxin contamination can occur in a crop growing in the field, or contamination may be introduced during harvest, storage and/or processing of the animal feed for use in raising monogastric and ruminal animals. Mycotoxins are fairly stable compounds often found in animal feed for monogastric and ruminal animals, and they are a known cause of a wide variety of deleterious effects in these animals. Pesticides are other common contaminants of animal feed. Endotoxins are not natural contaminants of feedstuffs. Feedstuffs can be contaminated with endotoxins when mixed with products of animal origin. Endotoxins are another type of toxin, of bacterial origin, which are commonly found in the gastrointestinal tract of livestock, and pesticides are commonly found in the foodstuffs fed to various types of livestock, and as a result, have been known to have toxic effects on livestock.

Mycotoxins are known to cause toxic, teratogenic, mutagenic, and carcinogenic effects, and have been linked to a depression of the animal's immune system. Furthermore, mycotoxins can affect different organs in an animal: urinary, digestive, nervous, reproductive, and immune systems, and as such, it makes it more difficult to establish a precise diagnosis once an animal is affected. The effects of mycotoxins, depends on the level of contamination, the presence of one or more toxins, the type of animal, its age, the time of exposure, genetic makeup, and its nutritional and health status at the time of exposure to contaminated feed.

The most dangerous mycotoxins affecting poultry are aflatoxin, ochratoxin, T-2 toxin, fumonisin, and deoxynivalenol, also known as DON. These mycotoxins, along with other trichothecene mycotoxins, can also affect monogastric and ruminants, to greater or lesser degrees.

Clays have historically been added to feed to solve the problem of mycotoxin contamination. Once bound by the clay in the gastrointestinal track, the mycotoxins are discharged in the animal's excrement with little to no harm to the animal. Another material, hydrated sodium calcium aluminosilicate clay, has also been added to animal feeds, and similarly, has proven successful in binding mycotoxins in the animal's digestive system, such that they may be safely discharged from the animal's body. More in particular, these clays have been found to act as enterosorbents that tightly and selectively bind these poisons in the gastrointestinal tract of animals, decreasing their bioavailability and associated toxicities.

Some toxins such as mycotoxins (e.g., T-2) can produce oral lesions in poultry and other animals by direct contact when the feed is ingested or after it has been absorbed through the intestinal wall and excreted through the saliva. Currently used toxin binders are not effective at binding to lipophilic toxins and typically are only effective at binding hydrophilic toxins. Oral lesions caused by direct contact of toxins are not inhibited by current products. More in particular, the T-2 toxin is known to cause lesions in the oral cavity and tongue of poultry, as a result of its caustic effect, which are oftentimes severe and sometimes deadly, upon contact with the tissue lining in an animal's mouth. Further exacerbating this situation is the fact that if the T-2 toxin finds its way to be absorbed inside the animal's blood/circulatory system may result in the toxin being subsequently excreted through the saliva of the animal in a recirculating pattern resulting in an increase of the aforementioned lesions.

Therefore a composition and/or method which provide a toxin binding capacity which may be safely mixed into animal feeds and capable of binding with mycotoxins in the animal's digestive tract would be highly desirable. It would be even more advantageous to provide a toxin binding system which may be safely mixed into animal feed and capable of binding with mycotoxins inside the animal's mouth as well as at the animal's gastrointestinal tract level. Yet a further benefit may be obtained by providing a toxin binding system which is also effective in binding other toxins such mycotoxins, endotoxins, and/or pesticides.

SUMMARY

In some embodiments, a composition and/or method may include a toxin binding system which may be safely and effectively mixed into animal feed and which may include novel combinations of one or more of an organoclay, an aluminosilicate clay, and a synthetic hectorite clay. In at least one embodiment, the toxin binding system is effective in binding other toxins, such as mycotoxins, endotoxins and/or pesticides, which may find their way into the gastrointestinal tract of livestock. In some embodiments, the binding composition may include organoclay, bentonite, hectorite, humic acid, and/or any combination thereof. In some embodiments, a method may include inhibiting and/or ameliorating a malady associated with a mycotoxin using a composition as described herein.

In some embodiments, a toxin binding system may include an amount of an organoclay and an amount of synthetic hectorite clay.

In some embodiments, a toxin binding system may include an amount of an aluminosilicate clay and an amount of a synthetic hectorite clay.

In some embodiments, a toxin binding system may include an amount of an organoclay, and amount of an aluminosilicate clay, and an amount of a synthetic hectorite clay.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. In some contexts, "configured to" may be a broad recitation of structure generally meaning performing the task or tasks during operation. As such, the component can be configured to perform the task even when a system is not currently in use.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "bentonite" as used herein generally refers to an absorbent aluminium phyllosilicate clay consisting mostly of montmorillonite.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "synthetic hectorite" as used herein generally refers to a rare soft, greasy, white clay mineral with a chemical formula of $Na_{0.3}(Mg,Li)_3Si_4O_{10}(OH)_2$.

The term "humic acid" as used herein generally refers to a principal component of humic substances, which are the major organic constituents of soil (humus), peat and coal. It is also a major organic constituent of many upland streams, dystrophic lakes, and ocean water. It is produced by biodegradation of dead organic matter. It is not a single acid; rather, it is a complex mixture of many different acids containing carboxyl and phenolate groups so that the mixture behaves functionally as a dibasic acid or occasionally, as a tribasic acid.

The term "monogastric" as used herein generally refers to an animal having a simple single-chambered stomach.

The term "mycotoxin" as used herein generally refers to a toxic secondary metabolite produced by organisms of the fungi kingdom, commonly known as molds.

The term "organoclay" as used herein generally refers to an organically modified clay (e.g., an organically modified phyllosilicate), derived from a naturally occurring clay mineral. By exchanging the original interlayer cations for organocations (typically quaternary alkylammonium ions) an organophilic surface is generated, consisting of covalently linked organic moieties.

The term "ruminant" as used herein generally refers to mammals that are able to acquire nutrients from plant-based food by fermenting it in a specialized stomach compartment (rumen) prior to digestion, principally through microbial actions.

As previously indicated, the compositions are directed to a mycotoxins binding composition. More in particular, the present mycotoxins binding composition may be formulated for mixture into animal feed which are used as a food source for farming/raising of monogastric and ruminal animals including, but in no manner limited to, poultry, swine, dairy and beef cattle, sheep, goats, horses, and fish. As previously stated, mycotoxin contamination can occur in crops growing in the field, or it can be introduced during harvest, storage and/or processing of the animal feed. Pesticides could also be found in feedstuffs. Endotoxins can contaminate feedstuffs, if they are mix with animal by-products (e.g., blood meal contaminated with endotoxins).

In some embodiments, a toxin binding system may include an organoclay. Organoclay may include an organically modified phyllosilicate, derived from a naturally occurring clay mineral. By exchanging the original interlayer cations for organocations (typically quaternary ammonium/surfactants) an organophilic surface may be generated, capable of binding a wider range of toxins than the original clay, including but not limited to, mycotoxins, such as derive from tricothecenes fungi, endotoxins, and pesticides.

In another embodiment of the present invention, a toxin binding system may include an aluminosilicate clay. In at least one embodiment, the aluminosilicate clay may include a sodium calcium aluminosilicate clay. In some embodiments, a toxin binding system may include a hydrated sodium calcium aluminosilicate clay, and in one embodiment, an activated hydrated sodium calcium aluminosilicate clay. Bentonite may be included as an example of an aluminosilicate clay.

As will be appreciated by those of skill in the art, both organoclay and activated hydrated sodium calcium aluminosilicate clay are lipophilic, and will bind fats, oils, and other lipids. As discussed above, organoclays and sodium calcium aluminosilicate clays have been utilized as an additive in animal feeds and have been found to be effective in binding with mycotoxins in the gastrointestinal tract of animals including but not limited to poultry, swine, cows, cattle, and fish. Each of these clays has been found to be effective in binding endotoxins and certain pesticides which could found their way into the gastrointestinal tract of animals. In some embodiments, neither organoclay nor activated hydrated sodium calcium aluminosilicate clay bind beneficial constituents inherent within or added to animal feeds, such as, amino acids, vitamins, minerals, antibiotics, pigments, coccidiostats, etc.

As noted above, both the organoclay and the activated hydrated sodium calcium aluminosilicate clay are lipophilic, and as such, neither of these clays are effective in binding to hydrophilic mycotoxins. As such, in at least one embodiment, a toxin binding system may include an amount of a hydrophilic clay. In one embodiment, the present system may include an amount of a synthetic hectorite clay, such as is described in detail in U.S. Pat. No. 3,586,478, which is incorporated herein by reference in its entirety. A synthetic hectorite clay may be readily dispersible in water or other aqueous solvents. In some embodiments, the composition may include naturally occurring hectorite.

As such, a toxin binding system may include a combination of both a lipophilic clay, namely, organoclay and/or sodium calcium aluminosilicate, and a hydrophilic clay (e.g., a synthetic hectorite clay). Therefore, the toxin binding system may be effective in binding mycotoxins present in the animal's gastrointestinal tract, such as via contaminated animal feed. A toxin binding system may be effective in binding water soluble mycotoxins, such as, by way of example only, T-2 toxin which must be bound in the animal's mouth and the gastrointestinal tract. An effective T-2 toxin adsorbent may diminish or prevent the adsorption of T-2 toxin at the intestinal level and reduce the oral lesions caused by T-2 toxin excreted through the saliva. In some embodiments, the toxin binding system may be effective in binding endotoxins and pesticides also present in the gastrointestinal track of the animal via contaminated feedstuffs and via bacterial growth.

In some embodiments, a toxin binding system may include one or more humic acids. In some embodiments, humic acids may be hydrophilic. Humic acids may bind one or more mycotoxins. The humic acid may form between about 0.5% and about 5.0% of the binding composition. In some embodiments, humic acid may be provided by Leonardite. The term humic acid is a generic name. Leonardite comes only from the states of Wyoming, North and South Dakota.

In some embodiments, a toxin binding system may include one or more types of bentonite. In some embodiments, bentonite may bind one or more mycotoxins. The different types of bentonite are each named after the respective dominant element, such as potassium (K), sodium (Na), calcium (Ca), and aluminium (Al). Bentonite usually forms from weathering of volcanic ash, most often in the presence of water. For industrial purposes, two main classes of bentonite exist: sodium and calcium bentonite. The bentonite may form between about 50% and about 75% of the binding composition.

In some embodiments, any number of the components discussed herein may be combined to form a toxin binding system. By combining multiple components discussed herein into a single composition, a composition which binds mycotoxins better than the individual components may be achieved. In some embodiments, the binding composition may include organoclay, bentonite, hectorite, humic acid (e.g., Leonardite), and/or any combination thereof. As can be seen by comparing the efficacy results from the different studies detailed in the Examples section, the composition tested appears to be greater than the sum of the components forming the composition.

In some embodiments, the bentonite may form between about 50% and about 75% of the binding composition. In some embodiments, the synthetic hectorite may form between about 0.5% and about 5.0% of the binding composition. In some embodiments, the organoclay may form between about 20% and about 40% of the binding composition. In some embodiments, the humic acid (e.g., Leonardite) may form between about 0.5% and about 5.0% of the binding composition.

EXAMPLES

Having now described the invention, the same will be more readily understood through reference to the following example(s), which are provided by way of illustration, and are not intended to be limiting of the present invention.

Example 1

In one embodiment, a toxin binding system may include an amount of an organoclay and an amount of a synthetic hectorite clay, each as described hereinabove.

In some embodiments, the toxin binding system may be as follows:

| Component | Amount (weight percent) |
| --- | --- |
| Organoclay | 80.0 to 99.9 |
| Synthetic Hectorite Clay | 0.1 to 20.0 |

Example 2

In another embodiment, a toxin binding system may include an amount of a hydrated sodium calcium aluminosilicate clay and an amount of a synthetic hectorite clay, each as described herein above.

In some embodiments, the toxin binding system may be as follows:

| Component | Amount (weight percent) |
| --- | --- |
| Hydrated Sodium Calcium Aluminosilicate Clay | 80.0 to 99.9 |
| Synthetic Hectorite Clay | 0.1 to 20.0 |

Example 3

In yet one other embodiment, a toxin binding system may include an amount of an organoclay, and amount of a hydrated sodium calcium aluminosilicate clay, and an amount of a synthetic hectorite clay, each as described hereinabove.

In some embodiments, the toxin binding system may be as follows:

| Component | Amount (weight percent) |
|---|---|
| Organoclay | 0.9 to 99.0 |
| Hydrated Sodium Calcium Aluminosilicate Clay | 0.9 to 99.0 |
| Synthetic Hectorite Clay | 0.1 to 20.0 |

Example 4

Presented herein below are tests results for various components used to form one of the compositions as well as the composition for the efficacy against various toxins. TABLE I depicts the efficacy of synthetic hectorite (Laponite) against Aflatoxin, Fumonisin, Ochratoxin, and Zearalenone. TABLE II depicts the efficacy of Humic acid (Leonardite P) against Aflatoxin, Fumonisin, Ochratoxin, and Zearalenone. TABLE III depicts the efficacy of bentonite (Myco-AD D-F) against Aflatoxin, Fumonisin, Ochratoxin, and Zearalenone. TABLE IV depicts the efficacy of organoclay (Myco-AD A-Z) against Aflatoxin, Fumonisin, Ochratoxin, Zearalenone, and Endotoxin. The organoclay may be formed from 64% original bentonite (e.g., about 64%) and surfactant used to modify the original clay surface ((e.g., about 36%) (e.g., ammonium quaternary)). TABLE V depicts the efficacy of a binding composition formed from the compounds tested in TABLES I-IV combined together against Aflatoxin, Fumonisin, Ochratoxin, and Zearalenone. TABLE VI depicts the efficacy of organoclay (Myco-AD A-Z) against pesticides (e.g., several different examples of known organochlorine pesticides). The organoclay may be formed from 64% original bentonite (e.g., about 64%) and surfactant used to modify the original clay surface ((e.g., about 36%) (e.g., ammonium quaternary)). TABLE VII depicts the efficacy of Bentonite (Myco-AD D-F) against pesticides (e.g., several different examples of known organochlorine pesticides). The organoclay may be formed from bentonite. As can be seen by comparing the efficacy results from the different studies the composition tested appears to be greater than the sum of the components forming the composition.

TABLE I

| SyntheticHectorite (Laponite) | | | | |
|---|---|---|---|---|
| | Aflatoxin | Fumonisin | Ochratoxin | Zearalenone |
| % Adsorption | 92.9 | 82.3 | 32.1 | 46.4 |
| | 94.9 | 86.0 | 33.6 | 49.0 |
| | 95.2 | 88.5 | 32.9 | 52.3 |

TABLE I-continued

| SyntheticHectorite (Laponite) | | | | |
|---|---|---|---|---|
| | Aflatoxin | Fumonisin | Ochratoxin | Zearalenone |
| % Adsorption Average | 94.3 | 85.6 | 32.9 | 49.2 |
| % Desorption | 0.3 | 66.1 | 26.0 | 27.1 |
| | 0.4 | 62.7 | 26.7 | 30.2 |
| | 0.4 | 66.4 | 26.9 | 29.0 |
| % Desorption Average | 0.4 | 65.1 | 26.5 | 28.8 |
| % Efficiency | 93.9 | 20.5 | 6.4 | 20.4 |

TABLE II

| Humic Acid (Leonardite P) | | | | |
|---|---|---|---|---|
| | Aflatoxin | Fumonisin | Ochratoxin | Zearalenone |
| % Adsorption | 69.0 | 33.4 | 39.2 | 57.3 |
| | 68.7 | 30.6 | 37.7 | 52.9 |
| | 68.3 | 30.2 | 41.0 | 54.7 |
| % Adsorption Average | 68.7 | 31.4 | 39.3 | 55.0 |
| % Desorption | 27.3 | 26.7 | 7.8 | 46.5 |
| | 29.2 | 26.1 | 6.9 | 40.2 |
| | 28.8 | 25.9 | 6.8 | 41.8 |
| % Desorption Average | 28.4 | 26.2 | 7.2 | 42.8 |
| % Efficiency | 40.3 | 5.2 | 32.1 | 12.2 |

TABLE III

| Bentonite (MYCO-AD D-F) | | | | |
|---|---|---|---|---|
| | Aflatoxin | Fumonisin | Ochratoxin | Zearalenone |
| % Adsorption | 99.7 | 56.4 | 30.1 | 11.6 |
| | 99.6 | 49.5 | 29.7 | 15.7 |
| | 99.5 | 54.6 | 30.2 | 12.5 |
| % Adsorption Average | 99.6 | 53.5 | 30.0 | 13.3 |
| % Desorption | 0.5 | 42.0 | 27.6 | 9.3 |
| | 0.5 | 39.9 | 26.5 | 10.5 |
| | 0.6 | 43.8 | 28.0 | 10.3 |
| % Desorption Average | 0.5 | 41.9 | 27.4 | 10.0 |
| % Efficiency | 99.1 | 11.6 | 2.6 | 3.3 |

TABLE IV

| Organoclay (MYCO-AD A-Z) | | | | | | |
|---|---|---|---|---|---|---|
| | Aflatoxin | Fumonisin | Ochratoxin | Zearalenone | Endotoxin (Run 1) | Endotoxin (Run 2) |
| % Adsorption | 93.8 | 86.9 | 91.3 | 98.0 | 99.6 | 99.7 |
| | 94.3 | 91.3 | 96.0 | 98.7 | 99.6 | 99.5 |
| | 93.5 | 91.9 | 93.5 | 98.4 | 99.5 | 99.5 |
| % Adsorption Average | 93.9 | 90.0 | 93.6 | 98.4 | 99.6 | 99.6 |
| % Desorption | 13.8 | 6.5 | 0.3 | 1.7 | 0.0 | 0.0 |
| | 11.6 | 6.9 | 0.4 | 1.7 | 0.2 | 0.0 |
| | 15.4 | 6.6 | 0.3 | 1.8 | 0.0 | 0.0 |
| % Desorption Average | 13.6 | 6.7 | 0.3 | 1.7 | 0.1 | 0.0 |
| % Efficiency | 80.3 | 83.3 | 93.3 | 96.7 | 99.5 | 99.6 |

TABLE V

Organoclay + Bentonite + Humic Acid + Synthetic Hectorite (MYCOTOP)

|  | Aflatoxin | Fumonisin | Ochratoxin | Zearalenone |
|---|---|---|---|---|
| % Adsorption | 99.1 | 97.1 | 97.7 | 99.5 |
|  | 99.9 | 98.5 | 98.2 | 99.6 |
|  | 99.9 | 97.3 | 97.5 | 99.2 |
| % Adsorption Average | 99.6 | 97.6 | 97.8 | 99.4 |
| % Desorption | 0.1 | 26.5 | 2.7 | 0.5 |
|  | 0.1 | 24.0 | 3.0 | 0.9 |
|  | 0.1 | 26.8 | 6.4 | 0.9 |
| % Desorption Average | 0.1 | 25.8 | 4.0 | 0.8 |
| % Efficiency | 99.5 | 71.8 | 93.8 | 98.6 |

TABLE VI

Organoclay (MYCO-AD A-Z)

|  | Heptachlor (Organochlorine) | Dieldrin (Organochlorine) | Diazinon (Organochlorine) | Malathion (Organochlorine) |
|---|---|---|---|---|
| % Adsorption | 72.8 | 85.6 | 90.0 | 94.4 |
|  | 70.4 | 89.4 | 88.0 | 96.4 |
|  | 79.5 | 88.1 | 86.5 | 93.6 |
| % Adsorption Average | 74.2 | 87.7 | 88.2 | 94.8 |
| % Desorption | 23.8 | 15.1 | 6.5 | 1.0 |
|  | 18.9 | 16.1 | 6.4 | 0.7 |
|  | 22.4 | 13.1 | 5.6 | 2.1 |
| % Desorption Average | 21.7 | 14.8 | 6.2 | 1.3 |
| % Efficiency | 52.5 | 72.9 | 82.0 | 93.5 |

TABLE VII

Bentonite (MYCO-AD DF)

|  | Heptachlor (Organochlorine) | Dieldrin (Organochlorine) | Diazinon (Organochlorine) | Malathion (Organochlorine) |
|---|---|---|---|---|
| % Adsorption | 90.4 | 85.5 | 32.2 | 27.6 |
|  | 91.2 | 86.9 | 34.4 | 24.3 |
|  | 91.1 | 85.8 | 35.6 | 29.2 |
| % Adsorption Average | 90.9 | 86.1 | 34.1 | 27.0 |
| % Desorption | 7.0 | 15.7 | 8.3 | 12.7 |
|  | 6.7 | 18.9 | 5.4 | 9.2 |
|  | 6.0 | 21.2 | 7.0 | 8.0 |
| % Desorption Average | 6.6 | 18.6 | 6.9 | 10.0 |
| % Efficiency | 84.3 | 67.5 | 27.2 | 17.0 |

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of inhibiting and/or ameliorating a malady associated with a mycotoxin, a pesticide, and an endotoxin, comprising:
   combining a composition with an animal feed, wherein the composition comprises:
      an organoclay;
      bentonite;
      synthetic hectorite; and
      Leonardite humic acid;
   providing the animal feed to an animal whereby the composition binds to at least one mycotoxin within the animal, at least one pesticide within the animal, and at least one endotoxin within the animal, wherein the composition is configured to bind to the at least one mycotoxin, the at least one pesticide, and the at least one endotoxin when the composition is exposed to the at least one mycotoxin, the at least one pesticide, and the at least one endotoxin associated with the animal, wherein the at least one mycotoxin comprises Aflatoxin, Ochratoxin, Zearalenone and Fumonisin, and wherein the at least one pesticide comprises Dieldrin, Diazinon and Malathion;
wherein the animal is a farmed animal.

2. The method of claim 1, wherein the farmed animal comprises ruminant animals.

3. The method of claim 1, wherein the at least one mycotoxin, the at least one pesticide, and the at least one endotoxin is biologically innocuous to the animal by the binding of the at least one mycotoxin, the at least one pesticide, and the at least one endotoxin to the composition.

4. The method of claim 1, wherein the bentonite comprises between about 50% and about 75% of the binding composition.

5. The method of claim 1, wherein the organoclay comprises between about 20% and about 40% of the binding composition.

6. The method of claim 1, wherein the synthetic hectorite comprises between about 0.5% and about 5.0% of the binding composition.

7. The method of claim 1, wherein the hectorite comprises between about 0.5% and about 5.0% of the binding composition.

8. The method of claim 1, wherein the composition is configured to bind to, on average, at least 86% of the at least one mycotoxin.

9. The method of claim 1, wherein the composition is configured to bind to, on average, at least 99% of the at least one endotoxin.

10. The method of claim 1, wherein the composition is configured to bind to, on average, at least 70% of the at least one pesticide.

11. The method of claim 1, wherein the composition is configured to bind to, on average, at least 86% of the at least one mycotoxin, wherein the composition is configured to bind to, on average, at least 99% of the at least one endotoxin, and wherein the composition is configured to bind to, on average, at least 70% of the at least one pesticide.

12. The method of claim 1, wherein the farmed animal comprises poultry, swine, cattle, sheep, goats, horses, and fish.

* * * * *